(12) United States Patent
Penchel et al.

(10) Patent No.: US 10,881,056 B2
(45) Date of Patent: Jan. 5, 2021

(54) BIOREACTOR FOR IN VITRO PLANT CULTURE

(71) Applicant: FIBRIA CELULOSE S.A., São Paulo (BR)

(72) Inventors: Ricardo Miguel Penchel, Guararema (BR); Jocemar Palauro dos Reis, Aracruz (BR); Mila Liparize de Oliveira, São José dos Campos (BR)

(73) Assignee: SUZANO S.A.

( * ) Notice: Subject to any disclaimer, the term of this patent is extended or adjusted under 35 U.S.C. 154(b) by 154 days.

(21) Appl. No.: 15/035,990

(22) PCT Filed: Nov. 11, 2013

(86) PCT No.: PCT/BR2013/000483
§ 371 (c)(1),
(2) Date: May 11, 2016

(87) PCT Pub. No.: WO2015/066779
PCT Pub. Date: May 14, 2015

(65) Prior Publication Data
US 2016/0270312 A1    Sep. 22, 2016

(51) Int. Cl.
*A01G 31/06*    (2006.01)
*A01C 1/02*    (2006.01)
(Continued)

(52) U.S. Cl.
CPC .......... *A01G 31/06* (2013.01); *A01C 1/02* (2013.01); *A01G 7/02* (2013.01); *A01G 7/045* (2013.01); *A01G 17/00* (2013.01); *A01H 4/005* (2013.01)

(58) Field of Classification Search
CPC ........ A01G 31/06; A01G 31/02; A01G 7/045; A01G 7/02; C12M 21/02; C12M 23/22;
(Continued)

(56) References Cited

U.S. PATENT DOCUMENTS 4,216,741 A    8/1980  Moss
4,889,812 A *  12/1989  Guinn ................... C12M 29/12
                                                                    435/286.7
(Continued)

FOREIGN PATENT DOCUMENTS

EP    2638798 A1    9/2013
ES    2 002 927 A6   10/1988
(Continued)

OTHER PUBLICATIONS

International Search Report issued in PCT/BR2013/000483 dated Apr. 14, 2014.

*Primary Examiner* — Peter M Poon
*Assistant Examiner* — Jeffrey R Larsen
(74) *Attorney, Agent, or Firm* — Arent Fox, LLP

(57) ABSTRACT

A bioreactor comprising: an upper container with transparent walls for the material being propagated, the container being provided with gas exchange diffuser to the external environment, humidifier, and artificial illumination; a lower container with transparent walls, having an aluminum tray and a point of water entry and/or nutrient medium, located in the bottom of the container; points of injection/removal of air/oxygen/carbon dioxide located in the lid; point of additional injection of carbon dioxide, close to the bottom of the upper container; hermetic connection device between the upper and lower containers for supply/drainage of the nutrient medium; a screen support for the material to be propagated; locking devices to hermetically close the upper container; and the lower container; and pneumatic drivers of the liquid nutrient medium between the upper container and the lower container.

3 Claims, 4 Drawing Sheets

(51) Int. Cl.
*A01G 7/02* (2006.01)
*A01G 7/04* (2006.01)
*A01G 17/00* (2006.01)
*A01H 4/00* (2006.01)

(58) Field of Classification Search
CPC ...... C12M 31/10; C12M 29/00; C12M 29/06; C12M 23/58
USPC ........... 47/62 R, 59 R, 62 A, 62 N, 60, 62 E; 435/292.1, 289.1
See application file for complete search history.

(56) References Cited

U.S. PATENT DOCUMENTS

| | | | | |
|---|---|---|---|---|
| 4,894,342 | A * | 1/1990 | Guinn | C12M 29/12 435/297.4 |
| 5,998,184 | A * | 12/1999 | Shi | C12M 23/08 435/176 |
| 6,067,750 | A | 5/2000 | Lai | |
| 9,125,351 | B2 * | 9/2015 | Wu | A01G 31/02 |
| 2010/0291674 | A1 * | 11/2010 | Beese | C12M 23/28 435/325 |
| 2014/0242689 | A1 * | 8/2014 | Ramazanov | C12M 27/02 435/298.1 |
| 2015/0329816 | A1 * | 11/2015 | Owens | C12M 23/46 435/298.2 |

FOREIGN PATENT DOCUMENTS

FR 2 779 028 A1 12/1999
WO WO-2012044239 A1 * 4/2012 ........... A01G 9/1033

* cited by examiner

US 10,881,056 B2

BIOREACTOR FOR IN VITRO PLANT CULTURE

CROSS-REFERENCE TO RELATED APPLICATION

This application is a National Stage entry of International Application No. PCT/BR2013/000483, filed Nov. 11, 2013. The disclosure of the prior application is hereby incorporated in its entirety by reference.

FIELD OF THE INVENTION

The present utility model relates to a bioreactor of the temporary immersion type for in vitro cultivation of plants, preferably a bioreactor used in a production system for eucalyptus micropiles on a large scale and high productivity.

FUNDAMENTALS OF THE UTILITY MODEL

The bioreactors used in the production technique of plant seedlings are equipment for the aseptic cultivation of plants in a permanent or temporary immersion system in a liquid or semi-solid nutrient medium. In general, a bioreactor comprises a set of containers containing compartments and accessories for the optimal management of key growth factors to maximize the performance of biological reactions. The use of bioreactors in the production of plants for the temporary immersion technique makes it possible to achieve higher growth rates and multiplication of crops through the continued use of liquid nutrient medium, preferably supplemented with the injection of air and provided with artificial lighting.

The demand for forest products and the need for good quality raw material have required high investments in the forestry sector, resulting in significant advances in the production process and in the techniques used which at have evolved from conventional cutting to modern vegetative propagation or micropropagation.

Consequently, genetic improvements and biotechnology have required the development of new equipment for the production of in vitro seedlings, aimed at enhancing the benefits of micropropagation and reduction of their inherent difficulties. Among these devices, bioreactors stand out as the realization of a controlled environment for cultivation, for the temporary or permanent immersion of cells, buds, embryos or any appropriate type of propagules for the creation of species of plants, for example, forestry on a commercial scale. In particular, the automation and the use on a large scale, of cultivation in a liquid medium for the in vitro propagation of plants has been considered the best strategy in overcoming the barriers imposed by the high cost of crop production in semi-solid media (gelled).

Bioreactors are primarily categorized according to the method of agitation and construction of the container, including aerator stirrer, rotating drum, rotating filter, bubble trap, simple or combined aeration and bubble column, air lifting component, porous membrane to oxygen, over-aeration component and type of temporary immersion.

Temporary immersion systems include bioreactors, which are the essential component of these systems, characterized by the size of the container, type of substrate culture, existence of computerized or simple immersion control timer, and further comprise a peristaltic pump, air pump or mechanical movement of the container to displace the liquid medium, the possibility of recycling the liquid medium and separation (or embedding) of the liquid medium reservoir relative to the cultivation container. Common features of bioreactors include transparent walls for the passage of light and verification of the plant development process, and the possibility of being sterilized in autoclaves.

The two main types of micropropagation bioreactors for plant cells and tissues in a liquid nutrient medium are the RITA type (Automated Temporary Immersion Container) and BIT type (Temporary Immersion Bioreactor).

The RITA type is characterized by an array of containers for the material to be propagated and for the liquid nutrient medium, and the overlapping operation and control of the factors influencing the process, performed in an automated manner. The main advantage of the RITA type is the maintenance of stable and uniform conditions throughout the process, while the main disadvantage is its complex and costly operation.

The simplest and least costly BIT type has disposal containers, side by side, and the duration of immersion periods with the absence of the liquid medium in the micropropagation container, wherein the alternating of these periods is performed by a common control timer. However, the BIT type, despite being less expensive and having a simpler operation, requires closer monitoring of the micropropagation process, which is not automated, in addition to requiring a much larger space for the tiling of the containers.

Exemplary automated and non-automated bioreactors are described, for example, in document US20040209346 which shows an intermittent immersion bioreactor consisting of a central pivoted mechanism whose operation is automated. Document WO2012061950 details an automated bioreactor to obtain a kind of Antarctic species which requires special and well controlled conditions for micropropagation. Document WO2012044239 describes a bioreactor consisting of a container comprising an upper compartment (for plant tissue to be propagated), and a lower compartment (for liquid nutrient medium) with the liquid being transported through a gas injection compartment, from the lower compartment to the upper compartment, in accordance with the programming of the immersion period. Document WO2012156440 describes a temporary immersion bioreactor system, in which each bioreactor is composed of two containers, the upper being intended for the material to be propagated, and the lower for the liquid nutrient medium which is transported to the upper container for the completion of the soaking cycle, with the latter system characterized by maximum utilization of space of the micropropagation environment. Despite the advances brought about by these bioreactors known in the state of the art, certain disadvantages can be perceived that negatively influence micropropagation, such as greater difficulty in placement/removal of the material to be propagated, less efficient movement of nutrient medium and fewer points of injection/withdrawal of gases, among other disadvantages.

Thus, we verify the need for a temporary immersion bioreactor in a liquid nutrient medium supplemented with air injection and carbon dioxide enrichment, providing photosynthetically active radiation to the container containing the propagated material, and that this bioreactor should be appropriate for micropropagation of forest plants, and have a shape and dimensions which maximize the space environment where the vegetative propagation is carried out, with simultaneous ease of access to the container of the material to be propagated.

SUMMARY OF THE UTILITY MODEL

The present utility model aims to provide a custom bioreactor to meet physiological demands for the vegetative propagation of forest species, preferably eucalyptus, allowing intensive production in a good standard of quality, uniformity and vigor of produced shoots, greater rooting of micropiles and better acclimatization, and early yield of clonal seedlings for industrial use on a large scale.

The present utility model is embodied in the form of a bioreactor (1) for in vitro cultivation of plants, of the temporary immersion type comprising: (i) an upper container (2) with transparent walls for the propagated material, preferably explants of eucalyptus, said container (2) being provided with (a) gas exchange diffuser to the external environment, (b) humidifier (12), and (c) artificial illumination (14), preferably of the LED type; (ii) a lower container (3) with transparent walls for the liquid nutrient medium, having an aluminum tray (15) and a point (13) of entry for water and/or nutrient broth, preferably located in the center of the bottom of said container (3); (iii) points (4) of injection/removal of air/oxygen/carbon dioxide located in the transparent lid (5); (iv) point (11) additional injection of carbon dioxide close to the bottom of said upper container (2); (v) means (6) for hermetic connection between the upper and lower containers for supply/drainage of the nutrient medium to and from the top container and means (6) forming a dripline connecting the bottom of said upper container and said lower container; (vi) screen support (7) for the material to be propagated, with the possibility of exchanging screens of different meshes; (vii) means (8) for locking the lid for hermetic closure of the upper container; (viii) means (9) for locking of the top container for hermetic closure over the lower container; and (ix) means (10) of pneumatic movement of the liquid nutrient medium between said upper container and said lower container.

DETAILED DESCRIPTION OF THE INVENTION

Figure 1:
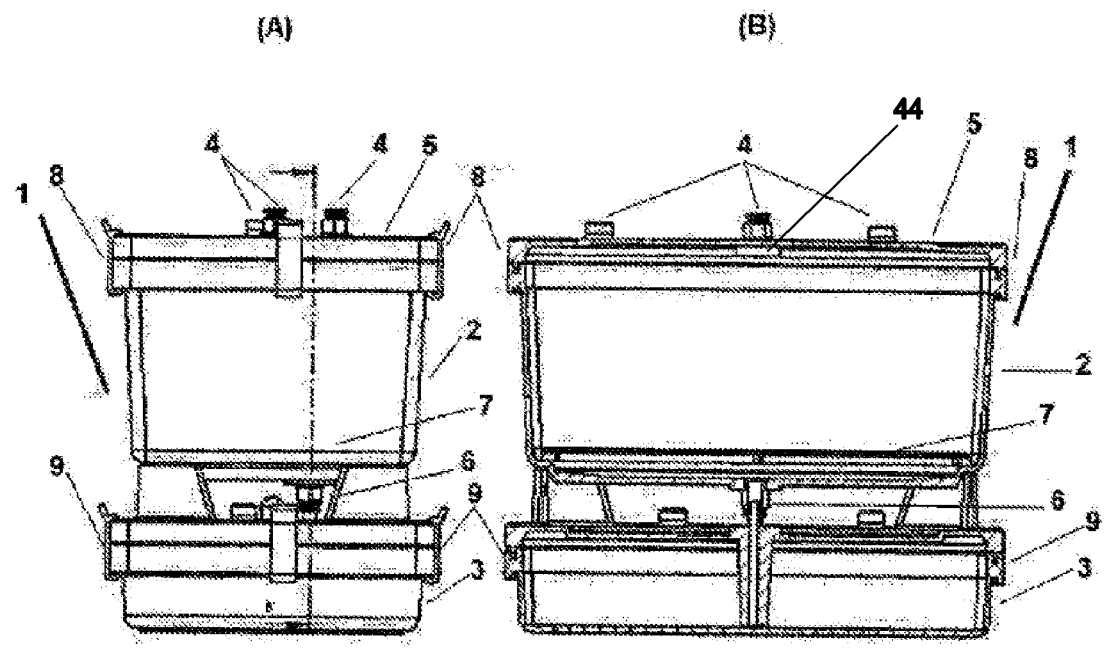
FIG. 1 shows a bioreactor according to the present utility model assembled, in (A) right-side view and in (B) front view.

There are various types of temporary immersion bioreactors on the market; the main ones being the RITA type (Automated Temporary Immersion Container), BIT type (Temporary Immersion Bioreactor), SIT type (Temporary Immersion System) and BioMint (Temporary Immersion Bioreactor) with a common, generally pneumatic operating concept of temporary immersion of the plants in the liquid nutrient medium. The great difference between them lies in the shape of the compartments for the plants and for storage of the liquid medium. In most of them, the plant growing containers are separated and individualized from the liquid medium storage compartment.

In the bioreactor, object of this utility model, the containers are coupled, one on top of the other, on a single platform, allowing reduction space. The great advantage of the bioreactor, BIT type, of the present utility model is its custom dimensions for the growth habit of tree species, mainly focusing on eucalyptus plantations. Furthermore, this bioreactor has unique features, such as valves and diffuser nozzles (points (4)), to allow gas exchange (air, oxygen, carbon dioxide, water vapor), to be controlled as needed by the culture. Additionally, artificial lighting is provided with lamps, preferably LED-type, to supply photons of light with light intensity and specific wavelengths to maximize photosynthetic rates, allowing increased carbon assimilation rates and subsequently their sequestration in plant biomass.

Thus, the bioreactor of this utility model can be used as a photoautotrophic production system, i.e., a system in which the plant grows without a carbohydrate source in the nutrient medium, where the environment is enriched with high photosynthetic radiation and high carbon dioxide concentration, thus resulting in higher growth rates and productivity, and higher survival of the plants.

The micro vegetative propagation carried out in the bioreactor of this utility model, compared to the production of seedlings in clonal gardens, enables better control of the microclimate and nutritional conditions of culture through a great and continuous supply of nutrients and growth regulators; renewal of the culture atmosphere with enrichment of gases; change and adaptation of the nutrient medium according to the demand of the plant at different stages of development, and control of microorganisms. The production of clonal seedlings of species and recalcitrant clones is an obstacle in conventional propagation because rejuvenation and/or reinvigoration of the matrices are not always achieved. Moreover, micro vegetative propagation allows the automation of the production flow, which reduces the need for extensive areas of conduits in clonal gardens, allowing greater production micropiles in reduced laboratory space and with greater efficiency in the use of energy and manpower employed in the multiplication of plants. Additionally, vegetative micropropagation allows the optimizing of operational aspects in the laboratory, since the plantlets are produced in large batches and with less handling of the plant material, thereby increasing the reliability for purity and cleanliness of the multiplied clones.

Figure 2:
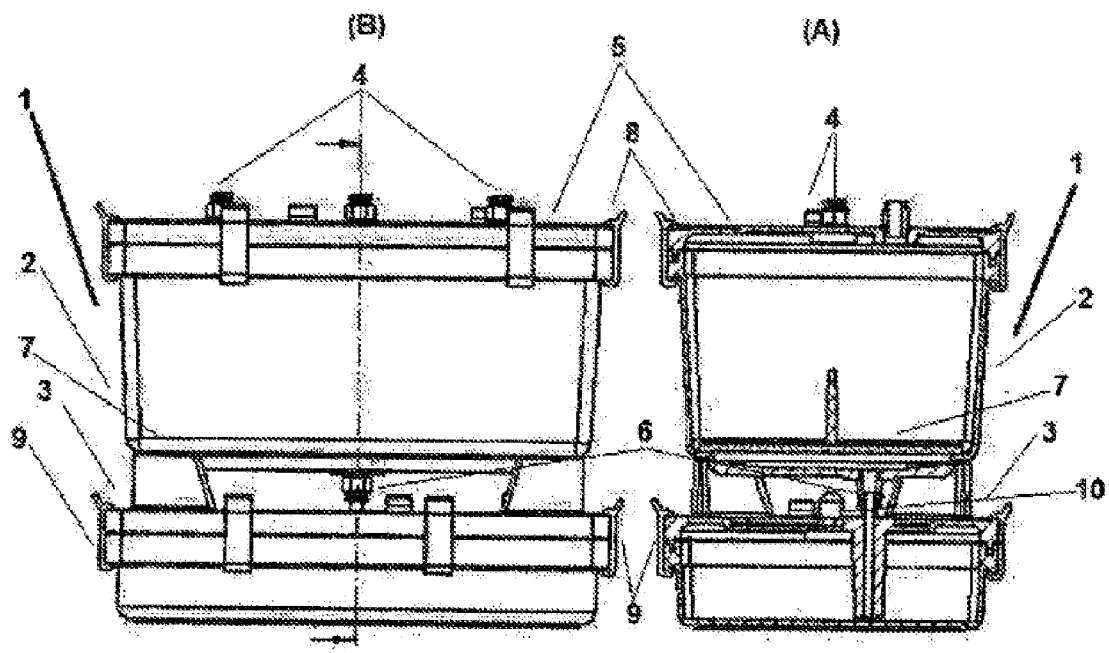
FIG. 2 shows a bioreactor according to the present utility model assembled, in (A) left side view and in (B) rear view.
Figure 3:
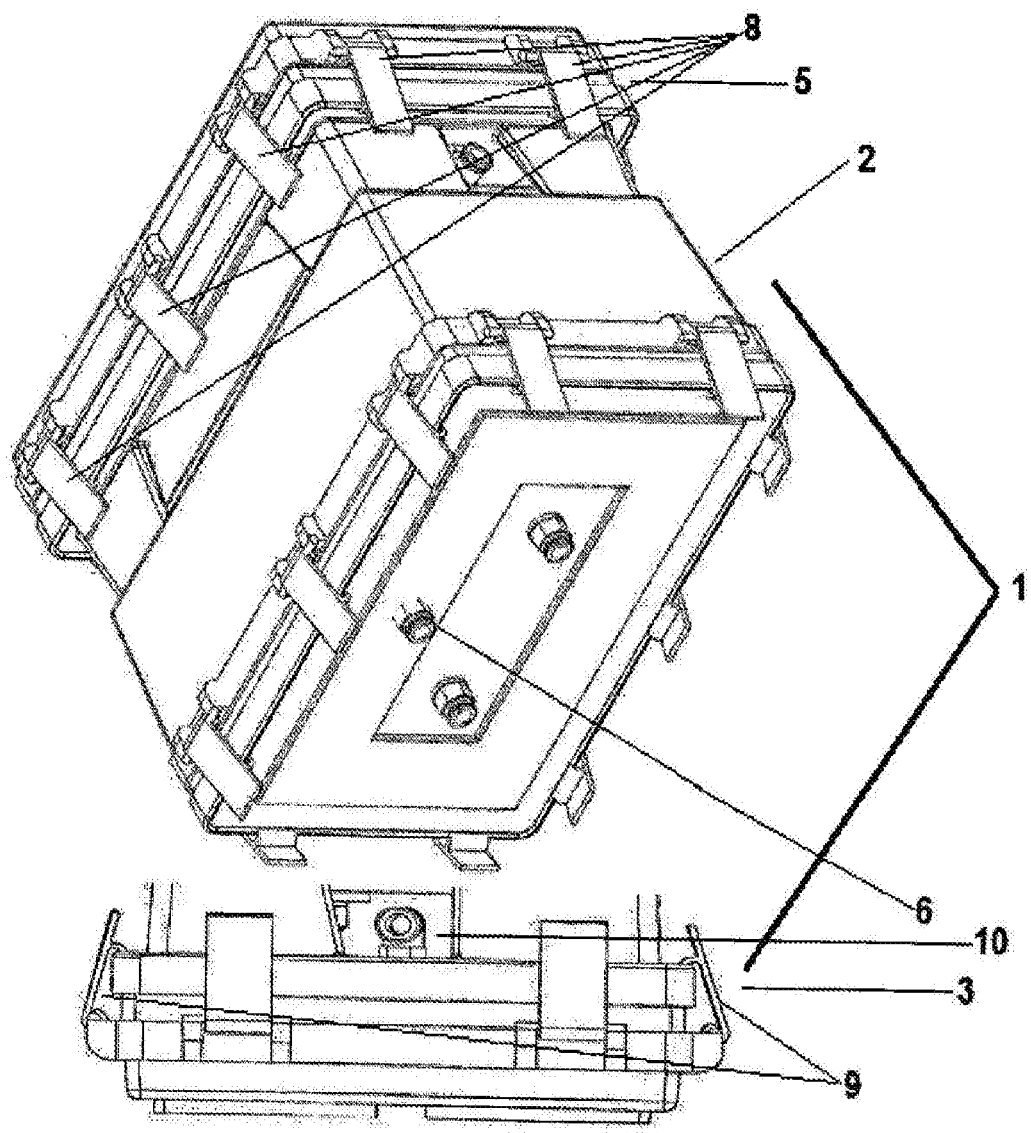
FIG. 3 shows a bioreactor according to the present utility model disassembled, in perspective, view seen from bottom to top.
Figure 4:
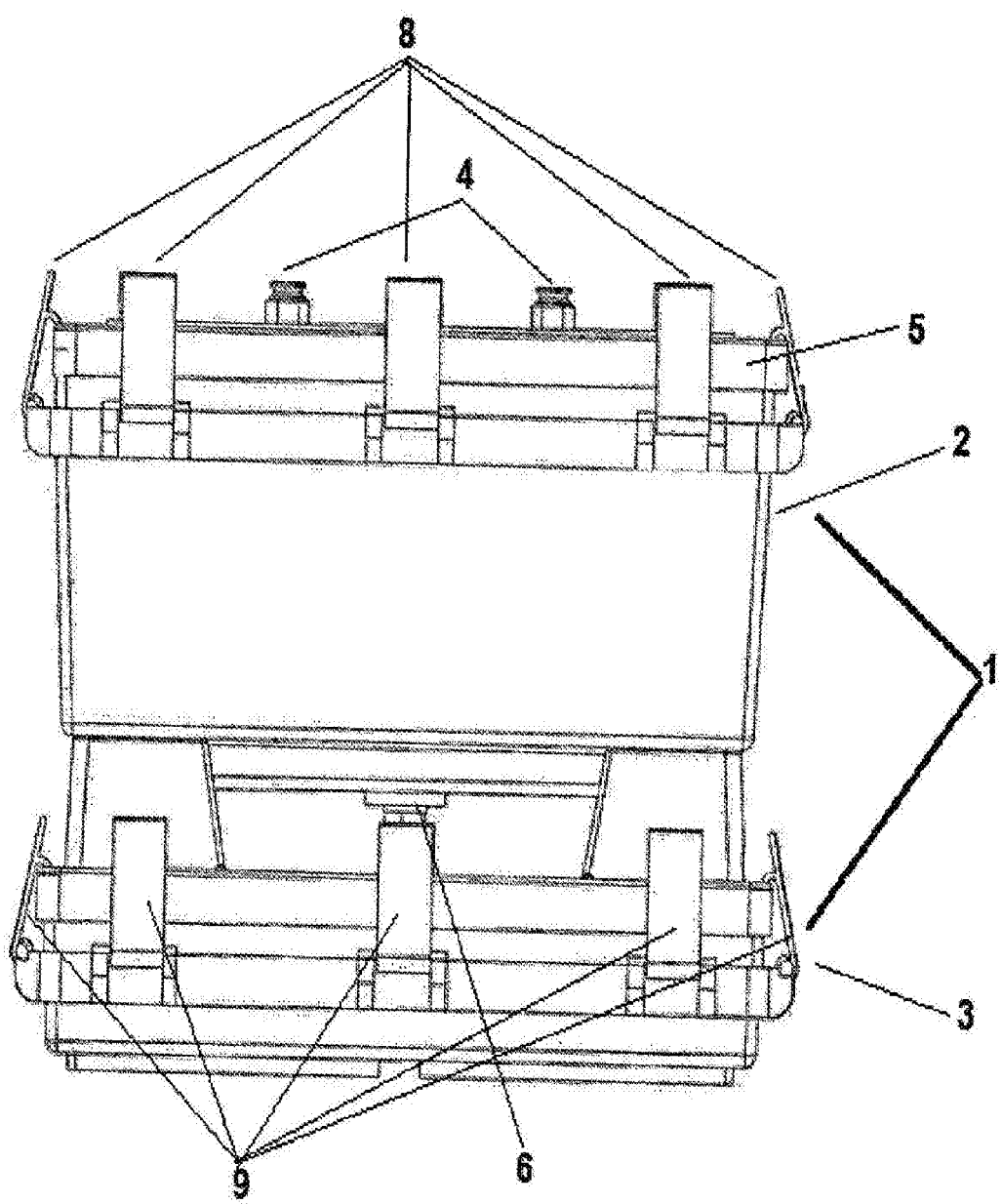
FIG. 4 shows a bioreactor according to the present utility model disassembled, in perspective, view seen from the front.
Figure 5:
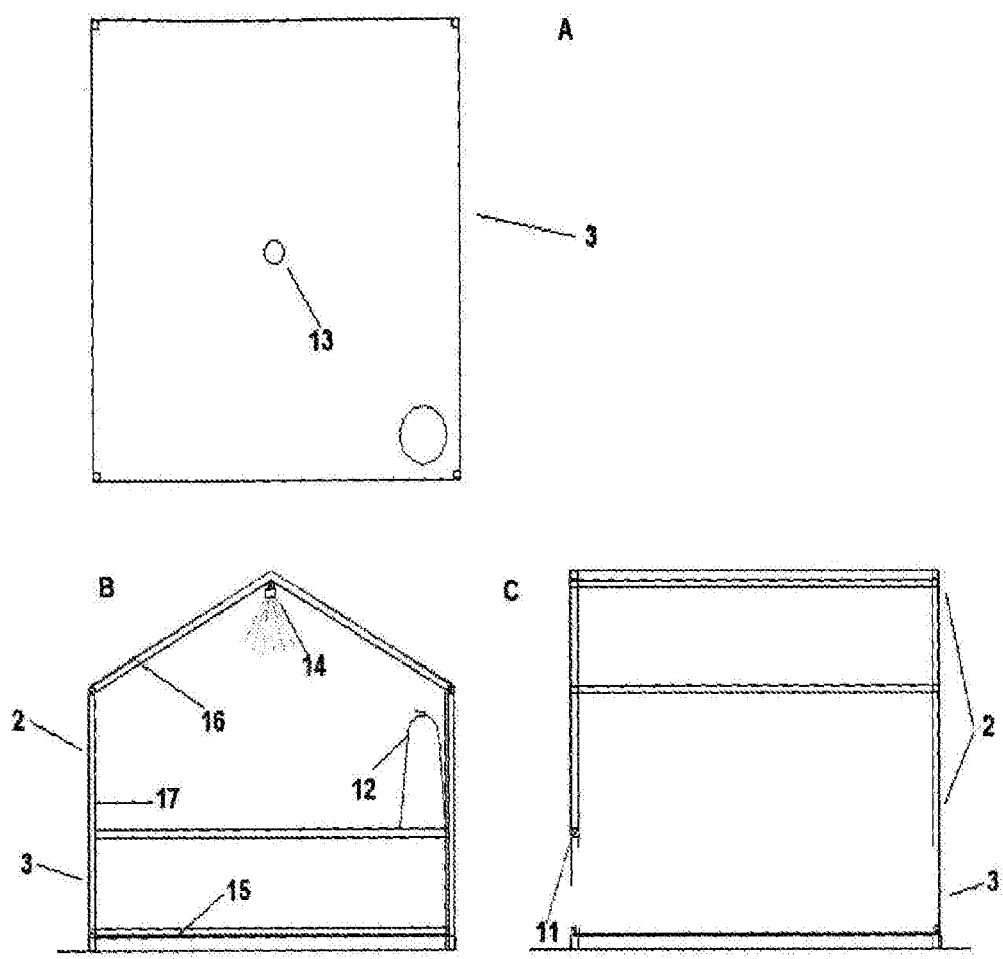
FIG. 5 schematically illustrates the bioreactor of the present utility model, with: (A) showing a bottom view of the container (3), (B) showing a front view of the bioreactor, and (C) showing a side view.

As shown in FIGS. 1 and 2, the bioreactor (1) of the present utility model comprises an upper container (2) for the propagated material and a lower container (3) for the nutrient medium destined for immersion of the material in vegetative propagation. The containers (2) and (3) have a suitable format to maximize space utilization in the environment for the micropropagation, for example, in a shape of a substantially rectangular or cubic box, preferably a rectangular box. The walls of the containers (1) and (2) are transparent and made of suitable material, not only to allow the passage of light, but also to respond positively to tests of biological functionality and structural and thermal resistance, for example, acrylic material of polyethylene, polypropylene, polycarbonate and glass, preferably with high mechanical strength.

The upper container (2) is provided with gas diffusers, made of suitable material, for instance metal or plastic, between the upper container and the external environment of the bioreactor to allow gas exchange of the plant culture with the external environment, and also to allow uniform enrichment of the top container with carbon dioxide injected through the top cover. The diffusers are fitted under pressure in holes with silicon gasket O-rings (44) on the inner side of the upper tank lid and additionally may be replaced by other larger gas flows, as required for the management of the internal atmosphere of the container.

The upper container (2) is provided with two or more points (4) of injection or drainage of air, oxygen, carbon dioxide and any gaseous substance that is to be controlled to allow for optimal air conditions for vegetative propagation. Said points (4) are located on the lid (5) of the top container, also aimed at avoiding the loss of lateral space between the bioreactors placed in parallel on shelves, and are achieved in the form of holes provided by means (6) of connection for example, by coupling, preferably threaded, of transparent gas pipes, said means being made from material resistant to sterilization conditions in an autoclave. Preferably, the means (6) have double locking silicone O-rings for sealing the coupling between the upper and lower containers.

Inside the upper container (2) is disposed a support (7), preferably made of a stainless steel screen with a polymeric frame material, for example nylon, to allow the exchange of screens of different meshes. Preferably, the support (7) is provided with rods, and is centralized, and another molded on the screen to facilitate the removal of all plant culture on the screen after the cultivation cycle. It is important to note that, according to the present utility model, preferably the support (7) comprises a thin stainless steel screen with different wire specifications (e.g., n° 6, n° 8, n° 10) and thick mesh (for example, n° 24, n° 26, n° 28) with no lower flanges, said screens being interchangeable to allow placement of different types of plant material (for example, nodal segments, shoot tips, isolated stems, isolated sprouts, multi-cap shoots, multi-sprout tufts).

The lid (5) may be positioned and locked on the container (2) in a sealed manner via a means of positioning and locking (8), which may hereinafter interchangeably be referred to as a first locking portion, to prevent contamination and to allow the operation of adequate supply and draining of the liquid nutrient medium to and from the container (2) for implementation of immersion periods. Similarly provided are also means (9) for positioning and locking the container (2) onto the container (3), which may hereinafter interchangeably be referred to as a second locking portion. Preferably, the means of positioning and locking (8) and (9) are provided with a sealing ring, preferably silicone, and sliding outer rail tabs injected on the upper container (means (8)) and lower container (means (9)). The outer safety locking tabs between the tops of the upper and lower containers additionally allow transport of the integrated assembly from one location to another without risk of disconnection between the containers. It should also be noted that the tabs have a double-locking characteristic, or double effect, giving the bioreactor of the present utility model the following advantages: (1) no need to press the two containers to seal the drain; (2) safety in all transport avoiding accident risks with the separation of the containers; (3) double-lock stage between the reservoirs, with the first being before the autoclaving assembly containers and culture medium, and the second after the autoclave thereof.

Additionally, the bottom container (3) has an inlet/drain (10) for compressed air for the pneumatic drive, which may hereinafter interchangeably be referred to as a driver, for carrying of the liquid nutrient medium from the containers (2) and (3). This pneumatic drive is provided with a timer (not shown) which is driven by a solenoid valve (not shown), alternating immersion periods (liquid transfer medium to the container (2) by increasing the pressure in the container (3)) and lack of immersion (liquid transfer medium to the container (3) for reducing the pressure in the vessel).

All parts of the upper container (2) and lower container (3) including lids, tabs, rods and screen frames are injected of polycarbonate resins, or equivalent polymeric material, translucent and smooth, with suitable strength properties to withstand successive autoclaving at 121 degrees Celsius and 1 atm for 40 min, e.g., in standardized conditions of temperature, pressure and duration. It is important to mention that the type of polymeric material used, preferably polycarbonate, should be such as to provide a reduction in bubble formation, conferring greater resistance to high injection pressures and resulting in less structural deformation in the temperature and pressure variations during the injection and discharge time in the manufacturing process.

The bioreactor of this utility model is appropriately sized to allow efficient micro propagation of tree species, preferably eucalyptus, while maximizing the use of space of the micropropagation environment. For example, the bioreactor may preferably have the dimensions of 300 mm length×200 mm width×250 mm in total height.

All publications and patent applications mentioned in this specification are indicative of the level of those skilled in the art to which the present utility model refers. All publications and patent applications are incorporated herein by reference to the same extent as if each individual publication or patent application were each specifically and individually indicated to be incorporated for ease of reference.

While certain embodiments have been described, they are only shown in an exemplary way, with no intention to limit the scope of the present utility model. The accompanying claims and their equivalents in this description are considered to cover such forms or modifications as they may be within the scope and spirit of the present utility model.

The invention claimed is:

1. A temporary immersion type bioreactor for in vitro cultivation of plants, the bioreactor comprising:
   i. an upper container with upper container transparent walls for material to be propagated, said upper container being provided with:
      (a) diffuser nozzles fit into holes arranged in said upper container, wherein the diffuser nozzles are provided with silicon gasket O-rings, wherein the diffuser nozzles are configured to allow for the injection or removal at least one of air, oxygen, or carbon dioxide,
      (b) a humidifier, and
      (c) an artificial illumination source;
   ii. a lower container for containing a liquid nutrient medium, wherein the lower container is enclosed via lower container transparent side walls, a top wall and a bottom wall, having a tray and at least one of a water or nutrient medium entry point, wherein the tray and the at least one of the water or nutrient medium entry point are located proximal to the bottom wall of said lower container;
   iii. an additional injection point for injection of carbon dioxide, wherein the additional injection point is located near a bottom of said upper container, and a dripline connecting the bottom of said upper container and said lower container;
   iv. a hermetic connection device for providing a connection between the upper and lower containers and for supply and drainage of the nutrient medium to and from the upper container;

v. a support having interchangeable screens of different meshes, configured to support the material to be propagated;
vi. a first locking portion for positioning and locking the lid, wherein the first locking portion is adapted to provide hermetic closure of the upper container;
vii. a second locking portion for positioning and locking the upper container onto the lower container, wherein the second locking portion is adapted to provide hermetic closure over the lower container; and
viii. a driver for moving the liquid nutrient medium, wherein the liquid nutrient medium is moved between said upper container and said lower container.

2. The temporary immersion type bioreactor of claim 1, wherein the artificial illumination comprises light emitting diode (LED)-type illumination.

3. The temporary immersion type bioreactor of claim 1, wherein the second locking portion comprises a silicone ring and sliding outer rail tabs, wherein the sliding outer rail tabs are injected on the lower container; and wherein the upper container does not share a common container wall with the lower container.

* * * * *